(12) United States Patent
Liland

(10) Patent No.: US 8,360,063 B2
(45) Date of Patent: Jan. 29, 2013

(54) APPARATUS FOR STABILIZING AN AIRWAY TUBE

(75) Inventor: Frode Liland, Stavanger (NO)

(73) Assignee: Laerdal Medical AS, Stavanger (NO)

( * ) Notice: Subject to any disclaimer, the term of this patent is extended or adjusted under 35 U.S.C. 154(b) by 814 days.

(21) Appl. No.: 12/299,027

(22) PCT Filed: Apr. 26, 2007

(86) PCT No.: PCT/NO2007/000147
§ 371 (c)(1),
(2), (4) Date: Feb. 11, 2009

(87) PCT Pub. No.: WO2007/123420
PCT Pub. Date: Nov. 1, 2007

(65) Prior Publication Data
US 2009/0229616 A1    Sep. 17, 2009

(30) Foreign Application Priority Data
Apr. 26, 2006 (NO) .................................. 2006 1891

(51) Int. Cl.
*A61M 16/00* (2006.01)
*A62B 18/08* (2006.01)
(52) U.S. Cl. .......... 128/207.11; 128/207.14; 128/207.17
(58) Field of Classification Search ............. 128/207.11, 128/207.14, 207.17
See application file for complete search history.

(56) References Cited

U.S. PATENT DOCUMENTS

| 4,683,882 | A | * | 8/1987 | Laird | 128/207.17 |
| 5,513,633 | A | * | 5/1996 | Islava | 128/207.17 |
| 6,010,484 | A | | 1/2000 | McCormick et al. | |
| 6,067,985 | A | | 5/2000 | Islava | |
| 6,810,878 | B2 | * | 11/2004 | Palmer | 128/207.17 |

FOREIGN PATENT DOCUMENTS

| WO | WO 9529727 | 11/1995 |
| WO | WO 9731669 | 9/1997 |

OTHER PUBLICATIONS

International Search Report for PCT/NO2007/000147 mailed Aug. 28, 2007.
Written Opinion for PCT/NO2007/000147 mailed Aug. 28, 2007.
Norway Search Report for NO 20061891 dated Jun. 12, 2006.

\* cited by examiner

*Primary Examiner* — Lynne Anderson
(74) *Attorney, Agent, or Firm* — Nixon & Vanderhye P.C.

(57) ABSTRACT

An airway tube holder (10) has a face plate assembly to fix an airway tube (24). The assembly comprises a face plate (20) for placement over the mouth of a patient. The face plate (20) has a channel (22) including an open end (23) and a closed end (26) in which the tube (24) is fixedly positioned. A tube holding block (30) is integrally mounted to the face plate (20). The block (30) has a securing means (38, 40, 41) mounted in the tube holding block (30). A clamp (41) is secured to a screw (40) of the securing means by a loop (44) encircling the screw (40). A folded strip (106) is attached to the end of a headband (18) so secure the holder to a patient, and forms hooked portions facing in opposite directions. The block (30) is flexible enough to absorb an over-tightening of the screw (40).

9 Claims, 5 Drawing Sheets

APPARATUS FOR STABILIZING AN AIRWAY TUBE

This application is the U.S. national phase of International Application No. PCT/NO2007/000147 filed 26 Apr. 2007 which designated the U.S. and claims priority to Norway Patent Application No. 20061891 filed 26 Apr. 2006, the entire contents of each of which are hereby incorporated by reference.

The present invention relates generally to an apparatus for stabilizing an airway tube, and more particularly to an airway tube holder having a V-shaped tube securing device whereby the airway tube is held in a positive secured manner within the tube holder after the tube is inserted in the patient, especially to the patient's trachea or to seal around the laryngeal inlet, so that the airway tube is fixedly mounted to prevent inadvertent movement after the tube has been properly positioned within the patient's airways, especially the trachea and larynx area.

DESCRIPTION OF THE PRIOR ART

Endotracheal tube devices and laryngeal tube devices are used under several conditions such as for ventilating a patient during anesthesia, for resuscitation, as well as during critical care not only in the hospital but also during the time when a patient is being transported.

It is well known in the art that various problems and difficulties are being encountered in providing suitable means for securing an airway tube in a simple and positive manner to the tube-holding device which is part of the mouthpiece of the face plate assembly.

Many types of securing arrangements have been tried in the prior art which very often included simply mounting the tube in place with adhesive tape to several areas of the patient's face. Some airway tubes were mounted in a face plate that included a bite block whereby the patient was required to grip the bite block with his or her teeth. However, other prior art tube holders have included locking means for securing the airway tube to the face plate of the tube holder.

For typical examples of prior art endotracheal tube holders one may refer to those disclosed in the following U.S. patents:
U.S. Pat. No. 4,867,154 issued to A. B. Potter, et al;
U.S. Pat. No. 4,832,019 issued to B. Weinstein;
U.S. Pat. No. 4,744,358 issued to G. E. McGinnis;
U.S. Pat. No. 4,537,192 issued to B. R. Foster;
U.S. Pat. No. 4,449,527 issued to D. L. Hinton;
U.S. Pat. No. 4,249,529 issued to J. Nestor, et al.,
U.S. Pat. No. 5,402,776 issued to S. T. Islava,
U.S. Pat. No. 5,513,633 issued to S. T. Islava,
U.S. Pat. No. 6,010,484 issued to McCormick et al.
U.S. Pat. No. 6,067,985 issued to S. T. Islava U.S. Pat. Nos. 5,402,776 and 5,513,633 of Islava provide a convenient and safe apparatus for securing an endotracheal tube. The apparatus has also since been further improved by the addition of V-shaped clamp piece snapped onto the inner end of the thumb screw, as shown in U.S. Pat. No. 6,067,985. The V-shaped clamp piece acting as a tube clamp between the inner end of the screw and the tube to increase the clamping surface acting on the tube. A stem is attached to the clamp, the stem extending parallel to the screw and acting to stabilize the clamp.

BRIEF SUMMARY AND OBJECTS OF THE INVENTION

The present invention defines an endotracheal tube holder formed with a face plate adapted to fit over the patient's mouth area below the nose and just above the chin, and with the extending longitudinal sides being arranged to cover the patient's lip area. An adjustable head strap is attached to slotted openings positioned adjacent the outer free edges of the face plate to allow adjustment from either side.

The face plate has an inverted, substantially L-shaped channel having an open end to receive an endotracheal tube which is positioned in an inwardly extended V-shaped portion of the channel. A mouthpiece that defines a bite block is fixedly mounted to the inner facing side of the face plate. The bite block is also provided with a V-shaped notch to correspond to the V-shaped portion of the channel.

On the outer side of the face plate is a positive tube securing means defined by a tube-holding block assembly having a L-shaped channel and V-shaped recess corresponding to the face plate, whereby the endotracheal tube can be first positioned in the patient's mouth and throat prior to mounting the tube holder. After the tube holder is positioned over the airway tube, securing means, comprising an actuating means such as a thumb screw, mounted to one side of the tube-holding block assembly, is adjusted to engage with the tube, thereby forcing the tube to become fixedly wedged in a locked position in the "V" portion that is defined by the holding block assembly.

The Islava apparatus has a channel to accommodate an endotracheal tube. However, new airway tubes have been developed that have a larger dimension, especially the Laryngeal Mask Airway, which is an airway device used for anesthesia and airway support. It comprises a tube, which is inserted blindly into the pharynx, forming a low-pressure seal around the laryngeal inlet and permitting positive pressure ventilation. There is also an airway device called the Combitube, which it is also a desire to be able to secure with the apparatus of Islava.

To achieve this, according to a first aspect of the present invention, the channel width has been increased substantially so that it will be able to hold all known types of airway breathing tubes.

Even though the clamp snapped onto the end of the screw, as per the later improvement of Islava, is functioning quite well, there has been found a potential for the clamp to loosen from the screw. This may happen if the screw is forcibly screwed too far out, so that the clamp is pressed against the inner wall of the face plate to such an extent that it is detached from the screw. If this happens there is a slight risk that the clamp may fall into the mouth of the patient and be a potential hazard.

Although, a considerable force has to be used to detach the clamp from the screw, it is a desire to avoid the potential risk associated with this if such a stressed situation should occur causing a paramedic to use this amount of force.

To avoid the risk of detachment of the clamp presenting a potential hazard to the patient, according to a second aspect of the present invention, the stem of the clamp has been provided with a loop that encircles the screw. If the clamp should detach from the screw it will still be retained by the interaction of the loop and the screw.

In Islava there is a piece of foam fastened to the inside of the apparatus by means of an adhesive. It has been found that the adhesive may deteriorate if the apparatus is stored at high temperatures over a longer period of time. When such an apparatus is put into use there is a potential that a paramedic may tear the foam off by accident. If this happens he has the choices between losing valuable time in retrieving a new apparatus or use the apparatus without the foam.

To avoid the risk of the foam being torn off due to deteriorated adhesive, according to a third aspect of the present invention, the adhesive has been replaced by in-molded rivets. In addition to avoiding the effects of deterioration, this results in an environmental friendly manufacturing process since the use of adhesives is completely avoided.

The Islava apparatus is shaped to ensure that even though the screw is tightened as far as possible by hand, the passage through the tube will remain at a certain minimum cross section. Nevertheless, excessive tightening may result in constriction of the passage through the airways tube to such an extent that the patient ventilation becomes less effective.

It is therefore suggested, according to a fourth aspect of the present invention, to use the inherent flexibility of the face plate, which conveniently is made of plastics, as a means for absorbing an excessive tightening of the screw. An excessive tightening could result in a restriction of the airflow through the tube to a degree that the patient may get less air than intended. In rare circumstances it may also possible to substantially block the tube so that the patient virtually gets no air. Consequently, the channel in the face plate will open up when the screw is forcibly tightened so that the tube is squeezed to a less degree. To this end the face plate is dimensioned and shaped to have certain target flexibility.

There is also, according to a fifth embodiment of the present invention, provided a special fastening of the slide stick, which is secured with a hook-fastener that is folded and sewn so that it can both hold the head strap secured when tightened, and also hold the slide-stick. According to Islava's apparatus there is a need for an extra component with an adhesive tape on to achieve both fastening of the slide stick and the head strap.

The characteristics and advantages of the invention are further sufficiently referred to in connection with the accompanying drawings, which represent one embodiment. After considering this example, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

With the above and related objects in view, the invention consists in the details of construction and combination of parts, as will be more fully understood from the following description, when read in conjunction with the accompanying drawings and numbered parts. U.S. Pat. Nos. 5,402,776 and 5,513,633 are included herein by reference.

DETAILED DESCRIPTION OF THE INVENTION

Figure 1:
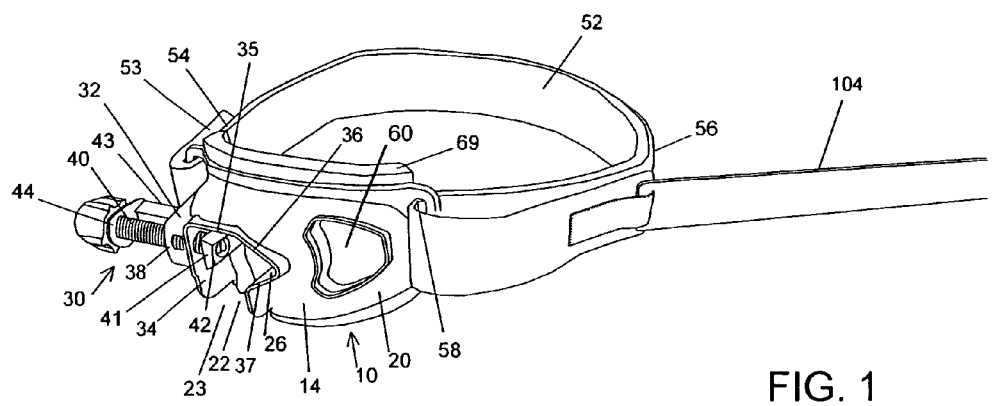
FIG. 1 is a pictorial view of an endotracheal tube holder of the present invention.
Figure 2:
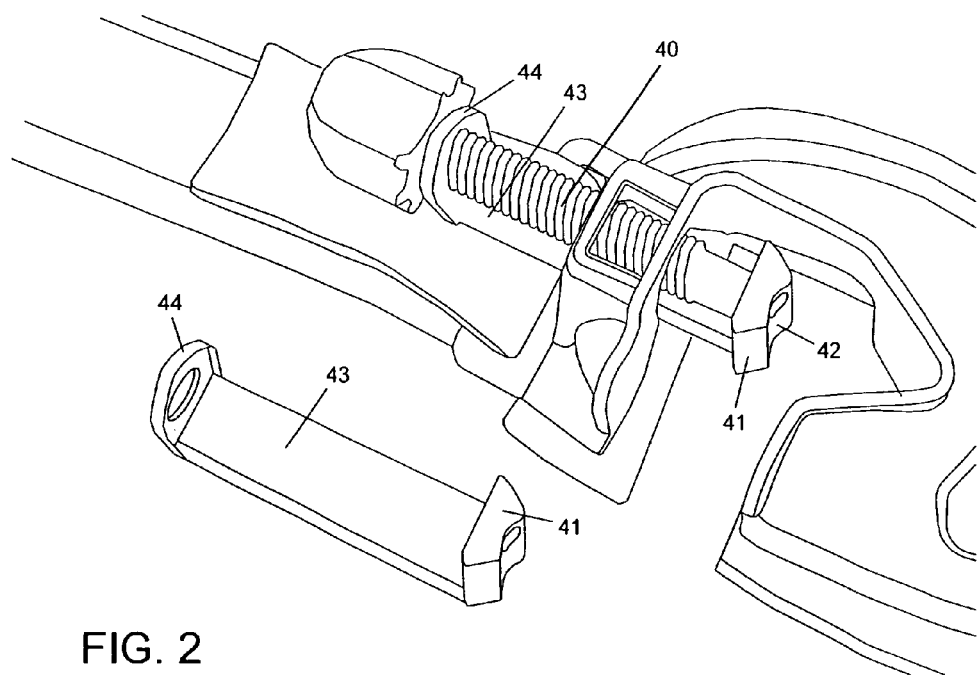
FIG. 2 is a detailed view of an aspect of the present invention showing the screw and clamp mounted in the face plate.
Figure 3:
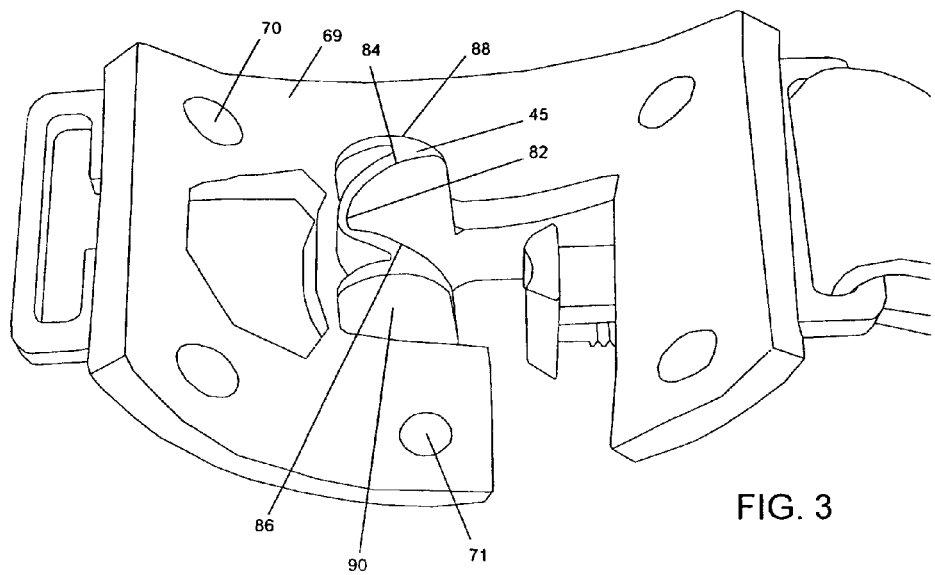
FIG. 3 is a rear view of the face plate showing the foam piece fasted by rivets.

Referring more particularly to FIG. 1, there is shown one embodiment of the present invention which is defined as an airway tube-holder apparatus, generally indicated at 10.

The airway tube-holder apparatus 10 is defined by a face-plate assembly, indicated generally at 14, which is adapted to be securely mounted to the patient's head by means of an adjustable attaching means 18, and will be hereinafter described in more detail. Face-plate assembly 14 comprises an elongated arcuate face plate 20 made of a suitable thermoplastic material adapted to be positioned over a patient's face so as to directly cover the mouth by means of the adjustable attaching means 18. The material from which the face place member is made should be sufficiently flexible to fit the contour of the patient's face. Face-plate member 20 is formed with a channel 22 which has a substantially inverted L-shaped configuration, the channel having an open end 23 to receive an endotracheal tube (see reference 24 in FIG. 4) and a closed end 26 in which the tube is to be fixedly secured.

The airway tube is generally positioned within the patient's mouth so as to be properly inserted within the trachea of in the laryngeal area. Once the airway tube 24 is properly positioned therein it should not be allowed to move longitudinally or to rotate. This is readily accomplished by mounting face-plate assembly 14 over the tube 24 by positioning the open end 23 of channel 22 to receive tube 24, whereby the tube 24 is further positioned within closed end of the channel 22 which is formed as a substantially V-shaped notch 26.

To provide a positive securing means for the airway tube there is integrally mounted to the outer surface of face plate 20 a tube-holding block assembly, designated generally at 30, which comprises a holding-block member 32 formed preferably from a suitable plastic material such as polyethylene which is integrally molded into face plate 20, as seen in FIGS. 1, 2, 3 and 4.

Figure 4:
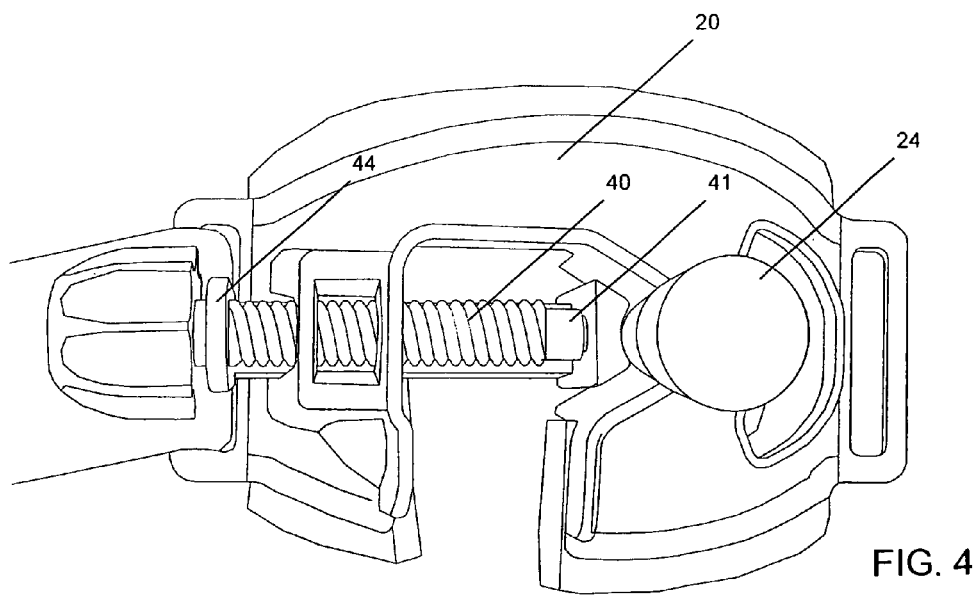
FIG. 4 is a front view showing an airway tube fasted in apparatus.
Figure 5:
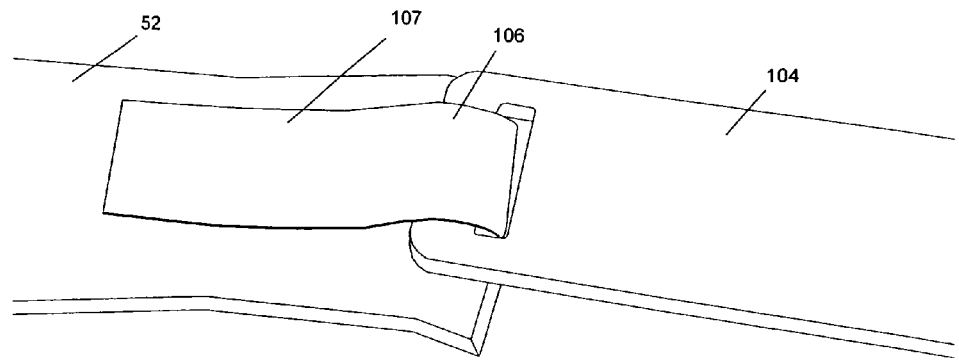
FIG. 5 a view showing the fastening of the slide stick or guide to the head band.

Holding-block member 32 is provided with a configuration that allows it to be superposed substantially over the perimeter of channel 22 of the face plate. Accordingly, the configuration of holding block member 32 comprises a vertical mounted wall 34, and an integral horizontal wall 35 which extends outwardly to establish a substantially V-shaped securing notch defined by a pair of converging wall members 36 and 37 adapted to receive an endotracheal tube 24 of any suitable size, as illustrated in FIG. 4. As can be seen from the figures the notches in the face plate and the holding block member are generally symmetrically about a horizontal axis.

Vertical wall 34 includes a threaded bore 38 in which is threadably mounted a thumb screw 40, also preferably formed from a suitable plastic material. At the inner end of the screw is mounted a clamp 41 (see FIG. 2) by snap-fitting. The clamp 41 has a groove 42 at the side facing the channel 22, the groove 42 being adapted to receive the tube 24 when the clamp 24 is pressed against the tube 24 by the tightening of the screw 40.

A stem 43 is integrally formed with the clamp 41 and extends parallel with the screw 40, through an opening (not shown) in the block member 32. At the opposite end of the stem 43 from the clamp 41 is integrally formed a loop 44, which is adapted to encircle the screw 40. The distance between the clamp 41 and the loop 44 is substantially the same as the length of the threaded portion of the screw 40.

If the clamp 41 is detached from the screw 40 at the snap-fitting, the loop 44 will ensure that the clamp 41 does not disengage fully from the screw 40. Thereby any risk for the clamp 40 falling into the mouth of the patient is effectively eliminated.

There is also provided a bite block 45 (se FIG. 3), having a substantially rectangular configuration, integrally mounted to the rear surface of face plate 20. Bite block 45 formed so that it has a V-shaped notch 82 defined by a pair of converging inclined walls 84 and 86. The outer or terminal ends of the walls 84 and 86 are joined to respective horizontal flexible walls 88 and 90 which extend rearwardly over the apex portion of the converging walls 84 and 86 as shown. This structure gives enough flexibility to the bite block 45 so that it can be firmly but comfortably grasped by the teeth without affecting the tube mounted therethrough.

It should be noted that face plate 20 is provided with an access opening 60 which permits various medical instruments to be passed through so as to be inserted into the mouth of the patient, as may be necessary.

The holding block member has been designed with a targeted flexibility in the walls 34, 35, 36, 37 thereof. This flexibility is sufficient to absorb the portion of the force from the screw exceeding the amount necessary to hold the airway tube securely in place and which can be achieved by hand tightening of the screw. Consequently, an over tightening of the screw resulting in an unintentional restriction of the passage through the tube is avoided.

Figure 6:
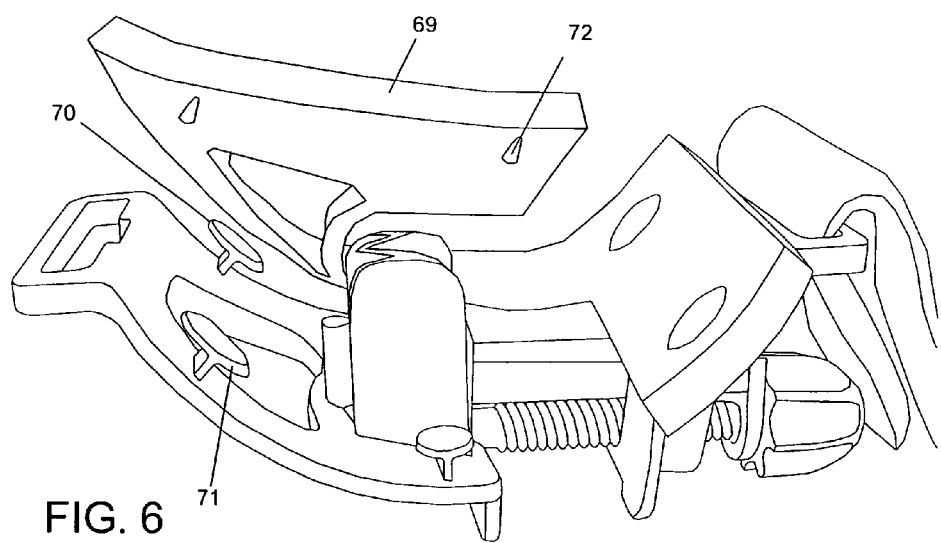
FIG. 6 is detailed view showing the in-molded rivets to secure the foam.

The face plate also includes a foam pad 69 on the internal face of the face plate so as to provide comfort for the patient. To fasten the foam pad 69 to the face plate 20, the rear side of the face plate 20 is provided with a plurality of integral rivets 70 (see FIG. 6), the rivets are generally T-shaped with a head 71 having generally oval surface facing the patient. The foam pad has openings 72 through which the rivets may be inserted. The heads of the rivets are larger than the opening 72.

The adjustable attaching means 18, as heretofore mentioned, comprises a headband that has an intermediate stretchable section defined by an elastic cloth strip 52 having a limited stretch capability to prevent the patient from readily removing the headband. Each end of intermediate elastic strip 52 has an interlocking strip of material 53, such as a hook-and-loop assembly.

Each oppositely disposed hook strip 54 is arranged to be inserted through slots 58 formed in face plate 20. Each hook section 54 is looped about its respective slot 58 so as to be adjustably connected to the corresponding loop strip 56.

Accordingly, both ends of the headband can be adjusted whereby the airway tube-holder apparatus can be properly positioned over the patient's mouth, as illustrated in FIG. 1. If desired, the entire headband may be made of a stretchable material having a limited stretch capacity.

When a patient is lying on his or her back, a thin elongated semi-rigid guide member 104 is attached to the head band 18. This allows the head band 18 to be positioned under the head or neck of the patient without the need to lift or move him or her. The guide member 104 is then removed and the head band is passed through slot 58 and then secured in place. The guide member 104 may be made of a suitable plastic material such as polypropylene.

Figure 7:
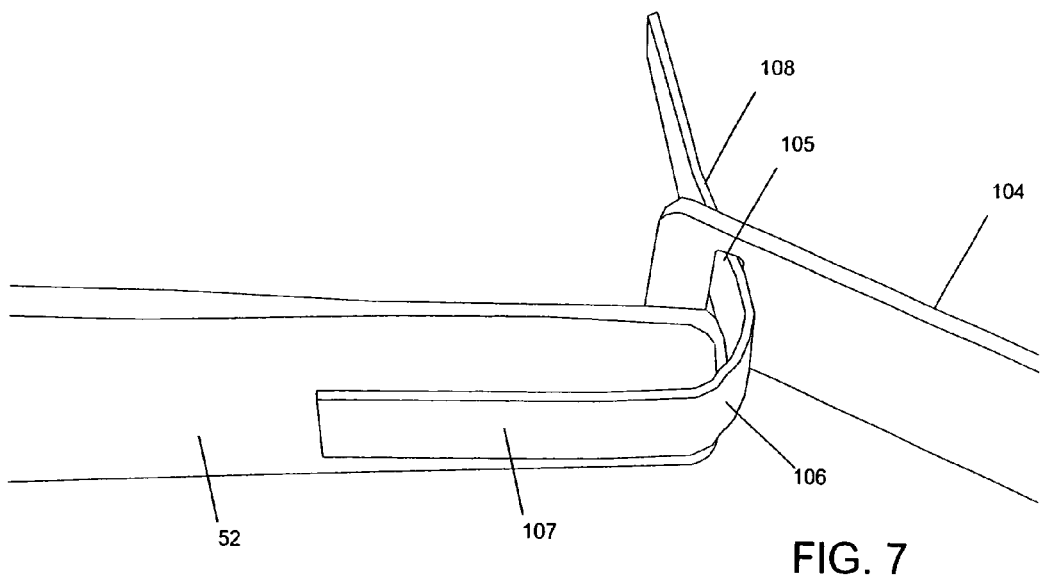
FIG. 7 is a detailed view of the fastening means for the headband guide.

FIG. 7 shows a new fastening means for the guide member 104. The guide member 104 has a slot 105 at the inner end thereof. At the end of the elastic strip 52 is fastened, preferably by sewing, a hook strip 106. The hook strip 106 is folded double at the portion 107, so that hooks are facing outward from the elastic strip 52 and towards the elastic strip 52. In the portion 108 extending from the end of the elastic strip 52, the hooks are thereby situated on the side facing the strip 52. Thereby the portion 108 can be fed through the slot 105 in the guide 104, bended towards the opposite side of the strip 52 relative to the portion 107 and fastened by means of the hooks to this opposite side of the strip 52. This way the same piece of hook fastener can be used to provide hooks (at the portion 108) for fastening the guide 104 and hooks (at the portion 107) for fastening the strip 52 to the face plate 20. To fasten the strip 52 to the face plate 20, the guide is detached from the strip 52 by opening the portion 108 and thread the hook strip and the elastic strip 52 through the opening 58 in the face plate and fold the portion 107 over the elastic strip 52 to fasten it thereto.

Figure 8:
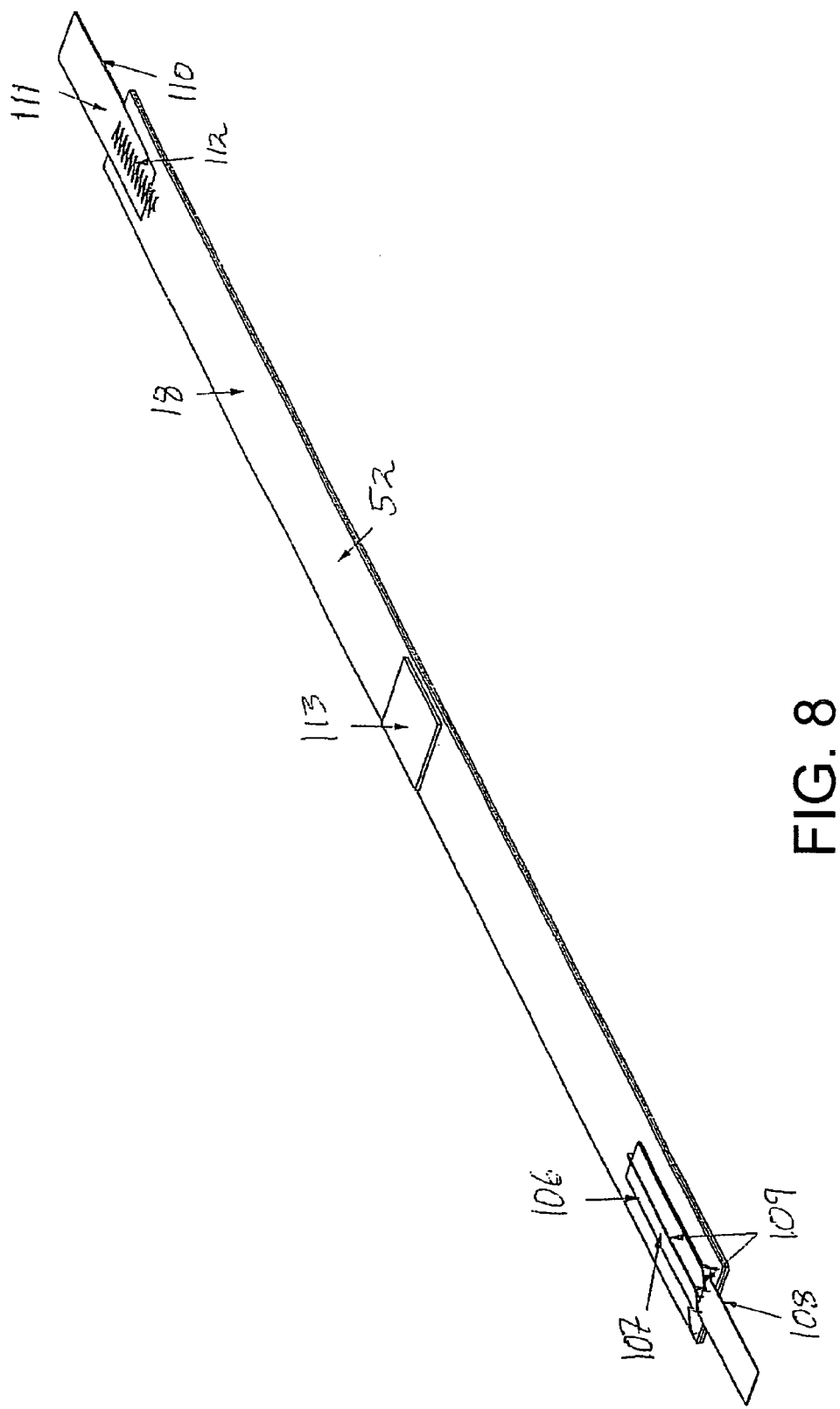
FIG. 8 is a detailed view of the headband.

FIG. 8 shows the headband 18 in a stretched out position. At the first end of the elastic band 52 is a hook strip 106, which is folded double at the portion 107 so that hooks are facing outward from the headband 18. At the portion 108, which protrudes from the elastic band 52, hooks are facing in the opposite direction, i.e. downward in FIG. 8. The hook strip 106 is preferably sewn to the elastic band by stitches 109. At the second end of the elastic band is a second hook strip 110. This hook strip is not folded and the hooks 111 are facing upward in FIG. 8, i.e. the same direction as the hooks of the portion 107. The hook strip 110 is preferably sewn to the elastic band 52 by stitches 112.

The head band also comprises a detachable hook strip 113 with hooks on both sides, to facilitate shortening of the headband 18 if necessary.

The foregoing should only be considered as illustrative of the principles of the invention. Further, since numerous modifications and changes may readily occur to those skilled in the art, it is not desired to limit the invention to the exact construction and operation as shown and described, and accordingly, all suitable modifications and equivalents may be resorted to, falling within the scope of the claimed invention.

The invention claimed is:

1. An airway tube holder having a face plate assembly so as to fixedly receive an airway tube therein, said face plate assembly comprising: an elongated face plate for placement over the mouth of a patient; said face plate having a channel formed to include an open end to receive the airway tube therethrough, and a closed end defined by a notch in which the airway tube is fixedly positioned; a tube holding block integrally mounted to the outer surface of said face plate, said tube holding block having a tube access opening and a tube holding notch for fixedly receiving said tube therein, whereby said tube holding block is superposed over said channel, said notch of said channel and said tube holding notch of said tube holding block being aligned with each other; a securing means operably mounted in said tube holding block for fixedly engaging said tube positioned in said tube holding notch, said securing means having an actuating means and a clamp means coupled to said actuating means, said clamp means being adapted to engage said tube upon securing said tube, characterized in that said clamp means is secured to said actuating means by a loop means encircling said actuating means, said loop means being fixedly coupled to said clamp means.

2. The airway tube holder of claim 1, characterized in that said securing means of said tube holding block comprises a thumb screw mounted to fixedly engage said tube positioned in said notch of said holding block and that said loop means of said clamp means is encircling said screw.

3. The airway tube holder of claim 2, characterized in that said clamp means and said loop means are integrally connected by a stem.

4. The airway tube holder of claim 1, characterized in that said clamp means and said loop means are integrally connected by a stem.

5. The airway tube holder of claim 3, characterized in that said stem has substantially the same length as a threaded portion of said screw.

6. The airway tube holder of claim 1, characterized in that said clamp means is snap-fitted to the end of the actuating means.

7. An airway tube holder having a face plate assembly so as to fixedly receive an airway tube therein, said face plate assembly comprising: an elongated face plate for placement over the mouth of a patient; a pair of vertical slots disposed adjacent the opposite ends of the face plate; and an adjustable mounting means comprising a headband having at least one securing strip that is adapted for mounting through at least one of said vertical slots of said face plate, said at least one securing strip comprising a plurality of hooks disposed on one surface thereof, and said headband comprising a plurality of loops to interlock with said plurality of hooks, characterized in that said strip is folded double at a portion which is fixed to the headband, so that the surface having hooks thereon is facing outward, thereby creating a first hooked portion partially overlapping the headband at one end thereof and facing away from the headband, and a second hooked portion, at a part of the strip extending from the end of the headband, and facing the opposite direction of the first hooked portion, wherein the second hooked portion is adapted to secure a guide means having a slot at one of its ends, by mounting said second hooked portion through said slot and folding said second hooked portion back to engage said headband.

8. An airway tube holder having a face plate assembly so as to fixedly receive an airway tube therein, said face plate assembly comprising: an elongated face plate for placement over the mouth of a patient, characterized in that the side of said face plate adapted to face the patient has in-molded rivets for securing a soft pad.

9. The airway tube holder of claim 8, characterized in that the in-molded rivets are generally T-shaped with a substantially flat enlarged head.

* * * * *